United States Patent [19]
Ogawa et al.

[11] Patent Number: 5,962,319
[45] Date of Patent: Oct. 5, 1999

[54] HUMAN-TH1-SPECIFIC PROTEIN, GENE ENCODING THE PROTEIN, TRANSFORMANTS, RECOMBINANT VECTORS, AND ANTIBODIES RELATED TO THE GENE

[75] Inventors: Kazuyuki Ogawa; Kazuya Tanaka; Kinya Nagata; Shoichi Takano, all of Kawagoe, Japan

[73] Assignee: BML, Inc., Saitama, Japan

[21] Appl. No.: 08/869,793

[22] Filed: Jun. 5, 1997

[51] Int. Cl.$^6$ .............................. C12N 15/12; C12N 5/10
[52] U.S. Cl. .................. 435/325; 435/320.1; 530/350; 530/395; 536/23.5
[58] Field of Search ................... 435/320.1, 325; 536/23.5; 530/350, 395

[56] References Cited
FOREIGN PATENT DOCUMENTS 8-166791  5/1996  Japan .............................. C12N 15/00

Primary Examiner—Thomas M. Cunningham
Attorney, Agent, or Firm—Knobbe, Martens, Olson & Bear, LLP

[57] ABSTRACT

An element for specifying the condition and type of immune-related diseases on the basis of the knowledge about the polarization of distribution of Th1/Th2 subsets of helper T cells. The element for specifying or correcting the polarization of the Th1/Th2 subsets is implemented by use of a recombinant vector, a transformant, a human-Th1-specific protein, and an antibody which uses the human-Th1-specific protein as an antigen. A human-Th1-specific gene is prepared and specified by a subtraction technique and is incorporated into the recombinant vector. The transformant is formed by transforming the recombinant vector. The Th1-specific protein is encoded by the gene derived from the transformant.

11 Claims, 7 Drawing Sheets lane 1 T48 product
2 No RNA
3 Luciferase (positive control)

lane:

1; 2P15  3; Jurkat  9; LCL-Nag
2; KND4  4; Molt-4  10; U937
         5; MT-2    11; K562
         6; TL-Mor  12; HEL
         7; CCRF-CEM 13; Hela
         8; Daudi   14; Hep-G2

---- CONTROL ANTIBODY
——— ANTI-T48 MONOCLONAL ANTIBODY

HUMAN-TH1-SPECIFIC PROTEIN, GENE ENCODING THE PROTEIN, TRANSFORMANTS, RECOMBINANT VECTORS, AND ANTIBODIES RELATED TO THE GENE

BACKGROUND OF THE INVENTION

1. Field of the Invention

The present invention relates to a Th1-specific-protein and a gene encoding the protein. More specifically, the present invention relates to a protein which is specific solely for human Type 1 helper T cells and which can be advantageously used as means for simply and promptly specifying variations in balance among helper T cell subsets intimately involved in immunological disorders, such as atopic diseases or the progression of AIDS. The present invention also relates to a gene which encodes this protein.

Further, the present invention relates to a recombinant vector which harbors the gene and is used for expressing it, as well as to a transformant which is transformed with the recombinant vector.

Furthermore, the present invention relates to polyclonal and monoclonal antibodies against the Th1-specific protein, and a hybridoma which produces the monoclonal antibody.

2. Description of the Related Art

Immunology has made a remarkable progress in recent years and has added a great contribution to various fields of medicine.

Studies of immunology have revealed that cytokines produced by macrophages or lymphocytes play the central role in promoting or suppressing every immunological reaction, such as infection immunity, tumor immunity, allergies, or anaphylaxis.

Mosmann and Coffman, et al. classified CD4$^+$ T-cell clones which are established from mouse spleen cells and can be cultured for a long period of time into two different types of subsets according to the difference between cytokines produced by the clones (Mosmann, T. R., et al., J. Immunol., 136, 2348 (1986)).

Specifically, they classified CD4$^+$ T-cell clones into the "T-helper 1 (Th1) subset" and the "T-helper 2 (Th2) subset": the former principally produces IL-2, IFN (interferon)-$\gamma$, and TNF (tumor necrosis factor)-$\beta$; and the latter principally produces interleukin 4 (IL-4), IL-5, IL-6, IL-10, and IL-13.

Although the existence of such subsets of helper T cells in humans was initially deemed dubious, it is now well accepted (Romagnani, S., Immunology Today 12, 256 (1991), etc.).

Nowadays, the nature and functions of the helper T-cell subsets Th1 and Th2 in mice or humans are becoming much more evident. In terms of biological significance, they have become of great interest as dominant cells which control different immunological reactions.

In many infectious diseases or immunological diseases, polarization is observed in the distribution of the Th1/Th2 subsets of lymphocytes of patients; i.e., an extreme bias arises in the distribution toward either one of the subset Th1 or Th2. Therefore, it is suggested that the nature of this polarization phenomenon may reflect the condition and type of the disease.

For example, the following are currently known: (1) in the case of Mycobacterium diseases, if immunological reactions with respect to Mycobacterium are mainly delayed-type hypersensitivity (DTH) reactions, the Th1 subset is dominant, whereas if the immunological reactions are chronic and progressive, the Th2 subset is dominant. (2) In the case of HIV diseases, the production of Th1-type cytokines is observed among many long-term nonprogressive HIV-infected patients. If polarization arises toward the Th2 subset, the symptoms of the diseases become progressive or fulminated. (3) With regard to patients having atopic diseases, if there arises polarization toward the Th2 subset, the diseases become aggravated.

SUMMARY OF THE INVENTION

In view of the foregoing, the primary object of the present invention is to provide means for specifying the condition and type of immune-related diseases on the basis of the knowledge about the polarization of the distribution of Th1/Th2 subsets (hereinafter referred to as Th1/Th2 imbalance).

The inventors of the present invention carried out extensive studies on the above-described problems. As a result, they found that if a protein specific for Th1 cells, a gene which encodes the Th1-specific protein, a protein specific for Th2 cells, and a gene which encodes the Th2-specific protein are identified and prepared, it becomes possible to provide means for specifying the condition and type of an immunity-related disease of interest through use of the proteins, genes, and antibodies to them. The present invention was completed on the basis of this finding.

The present invention is directed to a protein specific for human Th1 cells and a gene which encodes the human-Th1-specific protein.

Specifically, according to a first aspect of the present invention, there is provided a human-Th1-specific protein having an amino acid sequence represented by sequence ID No. 6.

According to a second aspect of the present invention, there is provided a human-Th1-specific protein which has an amino acid sequence corresponding to an amino acid sequence represented by sequence ID No. 6 partially deleted, replaced, or added, and which has substantially the same biological activities as those of the human-Th1-specific protein.

According to a third aspect of the present invention, there is provided a human-Th1-specific gene which contains a nucleotide sequence coding for the amino acid sequence represented by sequence ID No. 6.

According to a fourth aspect of the present invention, there is provided a human-Th1-specific gene containing a nucleotide sequence represented by sequence ID No. 5.

According to a fifth aspect of the present invention, there is provided a human-Th1-specific gene which contains a nucleotide sequence corresponding to a nucleotide sequence represented by sequence ID No. 5 partially deleted, replaced, or added; which hybridizes with DNA having the nucleotide sequence represented by sequence ID No. 5 under stringent conditions; and which encodes a human-Th1-specific protein having substantially the same biological activities as those of a human-Th1-specific protein having the amino acid sequence represented by sequence ID No. 6.

According to a sixth aspect of the present invention, there is provided a recombinant vector for expressing a gene, which vector contains the human-Th1-specific gene as defined in any one of the aforementioned third to fifth aspects.

According to a seventh aspect of the present invention, there is provided a transformant which is transformed by the recombinant vector defined in the sixth aspect and in which the human-Th1-specific gene contained in the recombinant vector is expressed.

According to an eighth aspect of the present invention, there is provided a polyclonal antibody which is prepared by immunizing the entirety or a portion of the human-Th1-specific protein defined in the first or second aspect and which does not exhibit immunoreactivity with respect to the human-Th2 proteins.

According to an ninth aspect of the present invention, there is provided a monoclonal antibody which takes as its antigenic determinant any portion of the human-Th1-specific protein defined in the first or second aspect and which does not exhibit immunoreactivity with respect to the human-Th2 proteins.

According to a tenth aspect of the present invention, there is provided a monoclonal antibody as defined in the ninth aspect, in which the immunogen of the antibody is a recombinant vector defined in the sixth aspect.

According to an eleventh aspect of the present invention, there is provided a hybridoma which produces the monoclonal antibody defined in the tenth aspect.

DESCRIPTION OF THE INVENTION

Figure 1:
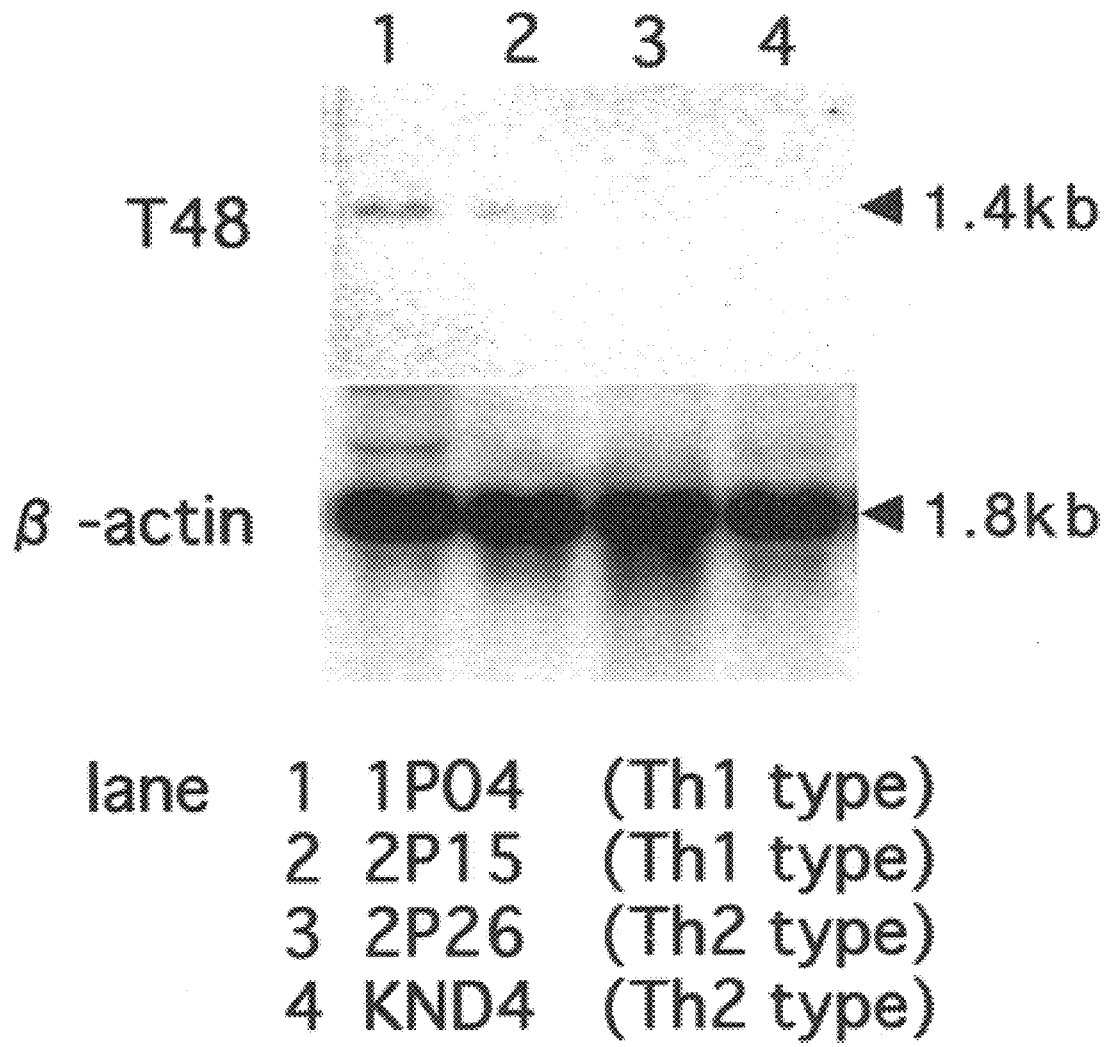
FIG. 1 is an autoradigram showing the results of a Northern blot analysis which indicate the Th clone selectivity with respect to mRNA expression derived from the Th1 gene of the present invention.

As described hereinabove, human Th1 from which human-Th1-specific gene used herein is derived is one of the subsets of human helper T cells. The human-Th1-specific gene will be hereinafter referred to as a Th1 gene. Unless otherwise specified, the Th1 gene includes an altered human-Th1-specific gene (which will be described below) that falls within the scope of the present invention.

The human Th1 is a subset of helper T cells having the following properties:

(1) The human Th1 cells produce IFN-γ and TNF-β but produces neither IL-4 nor IL-5.

(2) The human Th1 cells proliferate in response to IL-2 and IL-12, and the induction of the human Th1 cells are suppressed by IFN-4. (The other subset (i.e., the human Th2 subset) proliferates similarly with IL-2, and also proliferates, as opposed to human Th1 cells, in response to IL-4. In addition, induction of Th2 cells are suppressed in the presence of IFN-γ.)

(3) A surface marker for the human Th1 cells which can be definitely distinguished from the human Th2 cells are not yet found. The human Th1 cells, like the human Th2 cells, have phenotypes of $CD44^{bright}$, $CD45RB^{dull}$, and $LECAM-1^{dull}$.

(4) As contrasted with the human Th2 cells, the human Th1 cells does not have activity of inducing production of IgE. Rather, the human Th1 cells suppress production of IgE by self-produced IFN-γ.

(5) The human Th1 cells induce antigen-specific DTH.

(6) The human Th1 cells exhibit resistance to intracellular parasitic bacteria and protozoa under certain conditions.

The Th1 gene of the present invention can be obtained by establishing human Th1 clones having the above-described characteristics and producing a cDNA library of the human Th1 cells from the thus-established human Th1 clones.

A. Establishment of the Human Th1 Clones:

As a preceding step for establishing desired human Th1 clones, a $CD4^+$ T-cell population which is known to contain these clones is produced.

The $CD4^+$ T cell population can be produced according to a conventional method disclosed, for example, in "Ginfranco, F. D. P., et al., J. Clin. Invest. 88, 346 (1991)."

More specifically, peripheral blood mononuclear cells may be separated from the whole blood of humans, and the thus-separated peripheral blood mononuclear cells may be stimulated by various T-cell-activators to thereby produce a desired $CD4^+$ T-cell population. The T-cell-activators may include; e.g., non-specific T-cell-activators such as kidney bean-derived phytohemagglutinin (PHA); cytokines such as IL-2, IL-4, or IL-12; or stimulus antigens such as PPD or mite extracts.

Prior to isolation of $CD4^+$ T cell clones, which will be described below, the $CD4^+$ T cell-containing population is preferably subjected to removal of elements other than the $CD4^+$ T cells; e.g., $CD8^+$ T cells. For example, there can be employed a method for concentrating only the $CD4^+$ T cells through use of magnetic beads coupled to anti-CD4 antibody.

After completion of the above-described induction process, the $CD4^+$ T-cell clones are isolated. They can be isolated according to methods known per se such as the limiting dilution technique.

More specifically, for example, cells are cultured in a 96-well microplate (0.5 to 10 cells/well) through use of a PHA and IL-2. The medium is replaced with a fresh IL-2-added medium every three to four days. The surface marker of the cells which have been ascertained to proliferate (normally within two to four weeks) is examined. $CD4^+$ T-cell clones can be isolated by selecting only the CD4-positive clones.

From among the thus-isolated $CD4^+$ T-cell clones, human Th1 clones of interest can be selected.

The human Th1 clones are selected from the $CD4^+$ T-cell clones according the known differences in properties between the human Th1 and human Th2 cells.

Specifically, for example, clones which produce IFN-γ in response to the stimulation of anti-CD3 antibody but do not produce IL-4 can be selected as the human Th1 clones. (In contrast, clones which produce IL-4 but do not produce IFN-γ are selected as the human Th2 clones.

B. Preparation of Human-Th1-specific cDNA:

With regard to the cDNA of the human Th1 and that of the human Th2, it is anticipated that there exist nucleotide sequences common to both types of cDNA and nucleotide sequences specific for the respective types.

To prepare cDNA specific for the human Th1 cells of interest on the basis of such an anticipation, it is advantageous to use a so-called subtraction method by which cDNA species common to the human Th2 and Th1 cells are eliminated from cDNA molecules of the human Th1 cells.

The subtraction method may include, e.g., a method reported by Davis et al., (Davis, M. M. et al., Proc. Natl. Acad. Sci. U.S.A., 81, 2194 (1984)).

This method is intended to concentrate cDNA clones specific for one of two cell types, through hybridization of the cDNA to be subtracted with a greatly excessive amount of cDNA or poly $(A)^+$ RNA derived from the other cell type, and the screening of the cDNA library through use of non-hybridized residual cDNA as a probe.

Since this method requires a large amount of poly $(A)^+$ RNA, the method will become disadvantageous if a large quantity of poly $(A)^+$ RNA is not readily available.

To overcome this problem, another method has already been reported which uses the PCR technique in order to carry out subtraction through use of a comparatively small amount of poly $(A)^+$ RNA as a starting material [e.g., a gene expression method (Wang, Z. and Brown, D. D., Proc. Natl. Acad. Sci. U.S.A., 88, 11505 (1991), etc.]. This method also is characterized by the amplification of cDNA serving as a starting material by use of the PCR method. This method has the advantage of providing the ability of cloning a very small amount of mRNA through repetition of the subtraction operation and the amplifying operation by PCR.

In general, culturing a large amount of normal $CD4^+$ T-cell clones and securing a large amount of mRNA which serves as a template of cDNA is difficult. For this reason, the present invention preferably employs the "gene expression screen method," for example, from among the aforementioned subtraction methods.

More specifically, cDNAs derived from human Th1 clones and human Th2 clones are prepared by publicly known methods (e.g., a method in which a reverse transcriptase is used, with poly $(A)^+$ RNA being employed as a template of cDNA), and the resultant cDNAs are amplified by PCR.

In amplifying cDNA, it is desirable to previously subject the cDNA to treatment with restriction enzymes or ultrasonic treatment so as to obtain cDNA fragments which are suitable in length for amplification according to the PCR method.

For example, specific primers which contain different nucleotide sequences respectively for the human Th2 and the human Th1 may be used as the PCR primers needed to amplify cDNA according to the PCR method. Usually, these specific primers are prepared by chemical synthesis. Since only the human-Th1-derived cDNA is amplified through use of a specific primer after the subtraction, this method has the advantage of minimizing the amplification of a trace amount of human-Th2-derived cDNA which may contaminate the human-Th1-derived cDNA.

In this case, it is necessary to previously connect linkers—which contain sequences capable of being annealed with the PCR primer—to both ends of the cDNA fragments. Therefore, in the aforementioned fragmentation, it is desirable to use a restriction enzyme which produces cDNA fragments having terminals capable of being linked with the linkers.

After the cDNA fragments derived from the human Th1 and Th2 clones have been attached to the linkers, fragments having a certain length are selected from among the cDNA fragments by suitable fractionation methods such as agarose gel electrophoresis. The thus-chosen cDNA fragments are amplified by PCR, whereby the amplified cDNA fragments can be used as a starting material.

With the thus-prepared cDNA fragments, a gene library containing the human Th1 gene of interest according to the present invention can be prepared by subtracting the cDNA fragments which have the nucleotide sequences common to the human Th1 and Th2 from the human-Th1-clone-derived cDNA fragments.

This selection may be performed by hybridizing a given quantity of human-Th1-clone-derived cDNA fragments with an excessive quantity of labeled cDNA fragments which are derived from the human Th2 clones. The cDNA hybridized with the human-Th2-clone-derived cDNA fragments can be eliminated according to the labels, and the remaining cDNA fragments can be handled as cDNA fragments based on the nucleotide sequence specific solely for the human Th1 cells.

The labels used herein are not limited to any particular labels, so long as they allow the use of the foregoing screening method. Needless to say, it is preferable to use means which enables easy labeling and easy removal of the label. In this respect, it is preferable to use a method in which cDNA fragments are labeled, for example, with biotin, and the resultant labeled cDNA fragments are caused to be adsorbed onto streptavidin.

The thus-screened cDNA fragments based on the nucleotide sequence specific only for the human Th1 are amplified again by the PCR method and then screened by the foregoing screening means. Through repetition of these processes, the cDNA fragments of interest can be concentrated and amplified.

A gene library containing the Th1 gene of the present invention can be obtained through use of the thus-prepared cDNA fragments.

The gene library can be prepared through use of a method known per se.

Briefly, the cDNA fragments are inserted into a suitable vector used for transferring a gene, and the vector is introduced into a corresponding host, thereby enabling preparation of a gene library of interest. Here, it is possible to check whether or not the cDNA fragments have been inserted into the vector by means of the color selection based on the activity of a lac Z gene in the vector.

The vector for introduction purposes is not particularly limited. For example, useful plasmids include pBluescript, pUC18, pBR322, pBGP120, pPCφ1, pPCφ2, pPCφ3, pMC1403, pLG200, pLG300, pLG400, etc; useful λphages include λgt10, or λZAPII, etc. In consideration of ease of handling, a plasmid which contains the lac Z gene as a selection marker is preferably used. More specifically, of the above-described vectors, pBluescript, pUC18, or pBGP120 is preferably used.

The gene library may alternatively be prepared through use of a commercially available gene library preparation kit.

C. Isolation of the Th1 Gene of the Present Invention:

cDNA clones containing the Th1 gene can be isolated by screening of the Th1 cDNA library prepared in the above-described manner.

To this end, a publicly known screening method may be used. For example, there are first prepared genes derived from a gene library which has been prepared in the previous-described manner and is based on a human-Th1-specific genes, and genes derived from a gene library which has been prepared separately and is based on a human-Th2-specific genes. These genes are labeled to form labeled probes, and the labeled genes are then hybridized with a replica of the gene library based on a human-Th1-specific genes. Subsequently, clones which hybridize with a probe of the human-Th1-specific genes but does not hybridize with a probe of the human-Th2-specific genes are selected by screening. The selected clones can be used for determining the nucleotide sequence of the Th1 gene of the present invention, as the clones harbor the Th1 gene of the present invention.

To ensure extra care, there may be determined clones to be used for determination of the nucleotide sequence of the Th1 gene, which will be described later, by comparison of expression patterns of mRNA through use of the Northern blotting technique in which the total RNA or poly $(A)^+$ RNA of the human Th1 cells and the human Th2 cells are used.

The nucleotide sequence of the Th1 gene of the present invention contained in the thus-prepared clones can be determined through use of a publicly known method.

The nucleotide sequence of the Th1 gene of interest can be determined through use of, for example, a Maxam-Gilbert method (Maxam, A. M., and Gilbert, W., Proc. Natl. Acad. Sci. U.S.A., 74, 560 (1977)), a genomic sequence method (Church, G. M. and Gilbert, W., Proc. Natl. Acad. Sci. U.S.A., 81, 1991 (1984)), a multiplex method (Church, G. M., and Kieffer-Higgins, S., Science, 240, 185 (1988)), a cycle sequence method (Murray, V., Nucleic Acids Res., 17, 8889 (1989)), or a dideoxy method (Sanger, F., et al., Proc. Natl. Acad. Sci. U.S.A., 74, 5463 (1977)).

Alternatively, as a matter of course, the nucleotide sequence may be determined through use of a nucleotide sequence automatic analyzer to which the principles of the foregoing methods are applied.

On the basis of the thus-determined nucleotide sequence of the Th1 gene, the Th1 gene itself can be obtained.

More specifically, provided that the cDNA of the human Th1 cells which serves as the source of the Th1 gene prepared in the above-described manner is used as a template, and that the DNA fragment containing the sequences on the 5'-terminal site or the 3'-terminal site of the Th1 gene determined in the above-described manner is used as a primer, the Th1 gene can be amplified in large quantity by the aforementioned PCR method.

Alternatively, a traditional method is also available in which the full length of the Th1 gene of the present invention is obtained by selecting a clone containing the Th1 gene out of the DNA gene library from the human Th1 cells, with a human Th1 gene fragment itself whose nucleotide sequence has been determined being employed as a probe.

Further, the Th1 gene of the present invention can be produced by chemical synthesis through use of a publicly known method such as a phosphite-triester method (Ikehara, M., et al., Proc. Natl. Acad. Sci. U.S.A., 81, 5956 (1984)). In addition, the Th1 gene can be synthesized through use of a DNA synthesizer to which the chemical synthesis method is applied.

The inventors of the present invention have realized the existence of an altered gene containing the nucleotide sequence of the Th1 gene whose nucleotides are partly deleted, replaced, or added by alteration (this altered gene has a homology of about 70% or more with respect to the intact Th1 gene). Such an altered gene also falls within the scope of the present invention.

A human Th1 gene which can fall within the scope of the present invention is a human-Th1-specific gene which hybridizes with DNA containing a nucleotide sequence represented by sequence ID No. 5 (which will be described later) under stringent conditions or conditions under which a hybrid between DNA is less apt to be formed in a system. More specifically, the conditions include the temperature of the system (the higher the temperature, the lower the likelihood of the hybrid being formed), the concentration of salt (the lower the salt concentration, the lower the likelihood of the hybrid being formed), and the concentration of a denaturing agent such as formamide (the higher the concentration of the denaturing agent, the lower the likelihood of the hybrid being formed). Further, the human-Th1-specific gene encodes a human-Th1-specific protein which has substantially the identical biological activities as those of a human-Th1-specific protein containing an amino acid sequence represented by sequence ID No. 6 (which will be described later).

The term "substantially identical" used herein signifies that with regard to biological activities the human-Th1-specific protein is qualitatively and/or quantitatively identical to human-Th1-specific protein for comparison.

Specific biological activities of the human-Th1-specific protein will be described later.

A gene can be altered in a desired way through use of a publicly known method; e.g., a so-called site-specific mutagenesis (Mark, D. F., et al., Proc. Natl. Acad. Sci. U.S.A., 81, 5662 (1984)).

A local Th1/Th2 balance of a disease can be checked through use of the Th1 gene of the present invention produced in the above-described manner.

Specifically, a local Th1/Th2 balance of a disease can be checked by extracting mRNA from local tissue of the disease, and measuring the level of expression of the Th1 gene in the tissue through use of; e.g., an RT-PCR method ("PCR Protocols, a Guide to Methods and Applications" Innis, M. A., et al., ed., Academic Press, San Diego, 1990).

As mentioned herein under the heading "Description of the Related Art," the checking of the Th1/Th2 balance allows more reliable ascertainment of variations in the symptoms of diseases to which a Th1/Th2 imbalance is of importance; e.g., HIV diseases, allergic diseases, or various infectious diseases.

Although, as a matter of course, the Th1/Th2 balance can be checked through use of polyclonal/monoclonal antibodies specific to the human Th1 cells, which will be described later, the foregoing checking means is effective in the case where the use of these antibodies is difficult; e.g., the case where the quantity of expression of the target protein is a trace amount.

D. Manufacture of the Human-Th1-specific protein of the Present Invention:

Through use of the thus-produced Th1 gene of the present invention, a recombinant human-Th1-specific protein (hereinafter referred to as a "human Th1 protein") can be manufactured. Unless otherwise specified, the human Th1 protein includes human-Th1-specific proteins which can be translated from the above-described altered gene. As a matter of course, these altered proteins which can be translated from the altered gene have substantially the identical biological activities as those of the unaltered human Th1 protein of the present invention.

The human Th1 protein of the present invention can be manufactured according to a conventional known gene recombination technique by use of the Th1 gene of the present invention.

More specifically, the Th1 gene of the present invention is inserted into a gene expression vector which is in such a form as to be able to express the Th1 gene of the present invention. The recombinant vector is transferred into a host whose properties correspond to those of the vector, whereby it is transformed. The human Th1 protein of interest can be manufactured by culturing the transformant.

Preferably, there is used herein a gene expression vector which usually possesses a promoter and an enhancer in the upstream region, and a transcription terminating sequence in the downstream region of the gene which is to be expressed.

Expression of the Th1 gene of the present invention is not limited to a direct expression system but may be accomplished in; e.g., a fused protein expression system which utilizes β-galactosidase gene, a glutathione-S-transferase-gene, or a thioredoxin gene.

Examples of gene expression vectors include vectors whose hosts are *E. coli* (e.g., pQE, pGEX, pT7-7, pMAL, pTrxFus, pET, or pNT26CII); vectors whose hosts are *Bacillus subtilis* (e.g. pPL608, pNC3, pSM23, or pKH80); vectors whose hosts are yeast (e.g., pGT5, pDB248X, pART1, pREP1, YEp13, YRp7, or YCp 50); and vectors whose hosts are mammal cells or insect cells (e.g., p91023, pCDM8, pcDL-SRa296, pBCMGSNeo, pSV2dhfr, pSVdhfr, pAc373, pAcYM1, pRc/CMV, pREP4, or pcDNAI).

These gene expression vectors may be selected in accordance with the purpose of expression of the human Th1 protein of the present invention. For instance, in a case where the human Th1 protein is intended to be expressed in large quantity, it is desirable to select a gene expression vector capable of choosing *E. coli, Bacillus subtilis,* or yeast as its host. In contrast, in a case where the human Th1 protein of the present invention is intended to be expressed even in a small amount so as to become active reliably, a gene expression vector capable of choosing mammal or insect cells as its host is preferably selected.

Although the existing gene expression vector can be selected as mentioned above, as a matter of course, a gene expression vector may alternatively be prepared according to the purpose of expression as required.

These recombinant vectors also fall within the scope of the present invention.

The transfer of the vector harboring the Th1 gene into a host cell and associated transformation can be carried out by means of a commonly employed method; e.g., a calcium chloride method or an electroporation method for the case of the vectors which choose *E. coli* or *Bacillus subtilis* as their host cell; or a calcium phosphate method, an electroporation method, or a liposome injection method for the case of vectors which choose mammal or insect cells as their host cell.

The human Th1 protein of interest is accumulated by culturing the thus-obtained transformants according to a commonly employed method (the above-described transformants also fall within the scope of the present invention).

A medium used in the cultivation can be selected according to the properties of the host, as required. For example, if the host is *E. coli,* LB or TB mediums can be used as required. Further, if the host is a mammalian cell, an RPMI1640 medium can be used, as required.

The human Th1 protein can be isolated or purified from the culture products according to a common method. For example, the human Th1 protein is isolated or purified from the culture products by various processing operations, utilizing physical and/or chemical properties of the human Th1 protein of the present invention.

More specifically, the isolation or purification of the protein can be accomplished through use of processing making use of a protein precipitant, ultrafiltration, gel filtration, high-performance liquid chromatography, centrifugal separation, electrophoresis, affinity chromatography using a specific antibody, or dialysis. These techniques may be used singly or in combination.

In this way, the human Th1 protein of the present invention can be isolated or purified.

In the Th1 gene expression system, the T cells or bone marrow cells isolated as a host from a patient can be utilized for so-called gene therapy by transforming the cells through use of the Th1 gene, and returning the resultant transformants to the patient.

In this case, virus vectors such as retroviruses or adenoviruses may be mentioned as the gene expression vectors.

The gene therapy which uses the foregoing transformants can be applied to patients whose diseases are principally due to a Th1/Th2 imbalance in which Th2 is dominant. More specifically, the transformants are administered to patients infected with HIV, patients with chronic infectious diseases, patients suffering cancers, or patients with immediate allergies. The Th2-dominant Th1/Th2 imbalance, which is the principal cause of these diseases, can be treated by gene therapy in which the administered transformants are caused to express human Th1 protein within the body of the patients.

E. Manufacture of an Antibody against the Human Th1 Protein of the Present Invention The present invention is also directed to an antibody against the human Th1 protein of the present invention.

The polyclonal antibody of the present invention can be manufactured from immune serum derived from animals which are immunized with the human Th1 protein serving as an immunogen.

The human Th1 protein used herein as the immunogen is not limited to any particular type of immunogen. As a matter of course, the human Th1 protein that is encoded by the Th1 gene [further including a Th1 gene having a nucleotide sequence partly altered] prepared in the above-described manner, can be used as the immunogen. Further, a partial peptide of the human Th1 protein is obtained through direct enzyme processing of the protein, chemical synthesis, or expression of part of human Th1 gene. The thus-obtained partial peptide can be also used as an immunogen during manufacture of the polyclonal or monoclonal antibody of the present invention.

Cell lines derived from an animal which is of the same species and strain as the animal to be immunized are transformed with gene expression vectors into which the human Th1 protein [including the human Th1 protein or its derivative of the present invention]. Subsequently, the thus-transformed cells are transplanted to suitable animal to be immunized, whereby the polyclonal antibody of the present invention can be prepared. Specifically, the transformed cells continuously form the human Th1 protein within the body of the animal to which the transformed cells have been transplanted, and an antibody against the human Th1 protein is produced in the serum. This antibody in the serum may be also used as the polyclonal antibody of the present invention (Nemoto, T., et al., Eur. J. Immunol., 25, 3001 (1995)).

As is the case with the transplantation of the transformed cells, the polyclonal antibody can be manufactured by direct administration to the animal of an expression vector which expresses the human Th1 protein by intramascular or subcutaneous injection such that the human Th1 protein is continuously produced within the animal (Raz, E., et al., Proc. Natl. Acad. Sci. U.S.A., 91, 9519 (1994)).

The monoclonal antibody of the present invention can be manufactured by the steps of producing hybridomas between myeloma cells and immunocytes of animals that are immunized in the same manner of manufacturing the polyclonal antibody, selecting clones which produce human-Th1-protein-recognizable antibodies, and culturing the thus-produced clones.

The animal to be immunized is not limited to any particular kind of animal. Mice and rats can be widely used. However, in the case of the manufacture of the monoclonal antibody, an animal is preferably selected in consideration of the compatibility of the animal with myeloma cells used for cell fusion.

Immunity can be induced by administering the immunogen to an animal to be immunized by a commonly-employed method; e.g., intravenous injection, intradermal injection, subcutaneous injection, or intraperitoneal injection.

More specifically, the immunogen is administered to the animal several times every two to fourteen days by the above-described means, together with an ordinary adjuvant as desired. As a result, immune serum useful for manufacturing the polyclonal antibody or immunocytes useful for manufacturing the monoclonal antibody; e.g., immunized spleen cells, can be obtained.

In the case of manufacture of the monoclonal antibody, the following may be used as a myeloma cell which serves as a parent cell to be fused together with the immunocyte; e.g., SP2/0-Ag14, P3-NS1-1-Ag4-1, MPC11-45, 6. TG1. 7 (all of which are derived from mice); 210. RCY. Ag 1. 2. 3. (which is derived from rats); and SK0-007, and GM15006TG-A12 (both of which are derived from humans).

The immunized cells can be fused with the myeloma cells by known methods, for example, a method reported by Kohler and Milstein [Kohler, G. and Milstein, C., Nature, 256, 495 (1975)].

Specifically, the cell fusion is carried out within an ordinary culture medium to which promoting agents such as dimethylsulfoxide has been added as required in order to improve the efficiency of fusion, in the presence of a known ordinary fusion accelerator such as polyethylene glycol (PEG) or Sendai virus (HVJ) to thereby prepare a hybridoma.

A hybridoma of interest may be isolated by culturing it in an ordinary medium for selection purposes; e.g., a HAT (Hypoxanthine, Aminopterin, Thymidine) medium. In other words, a hybridoma of interest may be isolated by culturing fused cells in the medium for a sufficient period of time to kill cells other than the hybridoma. The thus-obtained hybridoma can be used for cloning by an ordinary limiting dilution technique and then selecting clones which produce the monoclonal antibody of interest.

A monoclonal antibody-producing strain of interest can be screened by a commonly-employed retrieving method; e.g., an ELISA method, a plaque method, a spot method, agglutination, an Ouchterlony test, or a RIA method.

The thus-prepared hybridoma which produces a human-Th1-protein-recognizable monoclonal antibody of interest can be subcultured in an ordinary medium or can be stored for a long period of time in liquid nitrogen (this type of hybridoma also falls within the scope of the present invention).

Monoclonal antibodies of interest are collected from the culture supernatant by culturing the hybridoma according to a customary method. Alternatively, the monoclonal antibodies are collected by administering the hybridoma to an animal having compatibility with the hybridoma so as to induce the hybridoma to proliferate, and collecting ascites from the animal.

Further, monoclonal antibodies of interest may be obtained by culturing immunocytes in vitro in the presence of the human Th1 protein or portions of the protein, preparing through use of the cell fusion means hybridomas between the immunized cells and myeloma cells after lapse of a predetermined period, and screening the antibody-producing hybridomas (Reading, C. L., J. Immunol. Meth., 53, 261 (1982); Pardue, R. L., et al., J. Cell Biol., 96, 1149 (1983)).

Monoclonal antibodies of interest can alternatively be manufactured through direct use of the Th1 gene or portions of the gene without use of the human Th1 protein as an immunogen.

More specifically, it is also possible to manufacture monoclonal antibodies which specifically recognize the human Th1 protein, by directly immunizing an animal through use of the Th1 gene [at this time, a gene expression vector containing the Th1 gene can be used as an immunogen], and by using immunocytes of the gene-immunized animal.

Details of methods making use of gene-immunization will be described in Examples below.

The thus-obtained polyclonal or monoclonal antibodies may be purified by ordinary means such as salting out, gel filtration, or affinity chromatography.

The thus-obtained polyclonal or monoclonal antibodies exhibit specific reactivity against the human Th1 protein of the present invention.

The polyclonal and monoclonal antibodies can be used as means for checking the Th1/Th2 balance within the body. In other words, the Th1/Th2 balance in the body is checked by determining the amount of human Th1 cells in a specimen through use of the antibodies in conjunction with ELISA, RIA, immunohistochemistry, flow cytometry, or the Western blotting technique. As mentioned in the section with the heading "Description of the Related Art," it becomes possible to more reliably ascertain variations in the symptoms of diseases to which a Th1/Th2 imbalance is of importance; e.g., HIV diseases, allergies, and various other infectious diseases.

The thus-obtained polyclonal and monoclonal antibodies may also be used as antibodies for correcting a Th1-dominant Th1/Th2 imbalance.

With regard to antibodies derived from animals, they are acknowledged to have antigenicity against humans if directly administered to humans. Thus, the animal-derived antibodies are not suitable for administration to humans. For this reason, a variable region of the gene of the animal-derived monoclonal antibody is subjected to cloning, and a gene of this variable region and a gene of the constant region in a gene of a human antibody are fused together. A fused antibody can be manufactured by inducing expression of the thus-fused gene (Clarkson, T., et al., Nature, 352, 624 (1991)).

This technique may be applied to the foregoing monoclonal antibody; namely, the fused antibody formed by fusion of the variable region of the animal-derived monoclonal antibody with the constant region of the human antibody can be also used as an antibody for correcting, for example, the Th1-dominant Th1/Th2 imbalance.

EXAMPLES

The present invention will next be described by way of examples, which should not be construed as limiting the invention.

EXAMPLE 1

Manufacture of a Th1 Gene of the Present Invention (1) Preparation of Helper T-cell Clones In order to chiefly induce human Th1 cells, 1 μg/ml of PHA (by EY laboratories), 50 ng/ml of rIFN-γ (by Genzyme), and 5 ng/m of rIL-12 (by R&D Systems) were added to the culture of peripheral blood mononuclear cells (PBMC) ($10^6$ cells/ml) isolated from a healthy human. The mixture was cultured for five days. Independently, in order to chiefly induce human Th2 cells, 2% (v/v) mite extract (by Torii), 20 ng/ml of rIL-4 (by Genzyme), and 5 μg/ml of monoclonal anti-IFN-γ antibody (by Genzyme) were added to the culture of PBMC, and the resultant mixture was cultured for five days.

After lapse of five days, 40 U/ml rIL-2 (by Shionogi) was added to each of the culture of PBMC. The PBMC were then further cultured for seven to ten days.

In order to isolate CD4+ T cells from the cultured cells, the cultured cells were adsorbed by magnetic beads (by Dynal) linked with anti-CD4 antibodies. The cells magnetically attracted to the magnetic beads were collected. The CD4+ T cells were dissociated from the magnetic beads by a magnetic bead separation reagent (by Dynal), whereby the CD4+ T cells were obtained.

Next, the thus-purified CD4+ T cells were transplanted to a 96-well microplate (0.5 cells/well) through use of RPMI 1650 supplemented with 0.5 μg/ml of PHA, 40 U/ml of rIL-4, and 15% of fetal bovine serum. The medium was replaced with a fresh IL-2-added medium every three to four days. The surface marker of the cells which were observed to have proliferated was examined by immunofluorescence. Only the clones which were positive with respect to the CD4 were selected, and the thus-selected clones were taken as CD4+ T-cell clones of interest (Gianfranco, F. D. P., et al., J. Clin. Invest., 88, 346 (1991)).

In order to examine the type of each of the CD4+ T-cell clones, the CD4+ T-cell clones (6×$10^5$ cells/300 μl/well) were cultured for 24 hours on a 48-well plate coated with an anti-CD3 antibody (OKT3: by Ortho Pharmaceutical). Concentrations of IL-4 and IFN-γ in the culture supernatant were measured by ELISA which uses the respective monoclonal antibodies.

As a result, the clones that produced IFN-γ but did not produce IL-4 were taken as human Th1 clones. The results are shown in Table 1.

TABLE 1

| Clone | Donor | Primary Stimulation | Cytokine production (ng/ml)[a] | | Th type |
|---|---|---|---|---|---|
| | | | IFN-γ | IL-4 | |
| 1P04 | KN | PHA | >50.0 | <0.2 | Th1 |
| 2P15 | KT | PHA | 19.2 | <0.2 | Th1 |
| 2P26 | KT | PHA | <0.5 | 9.0 | Th2 |
| KND4 | KN | Der[b] | <0.5 | 4.9 | Th2 |

[a] The cells (6 × $10^5$ cells/300 μl/well) were cultured for 24 hours in a 48-well plate to which OKT3 had been immobilized. Concentrations of IFN-γ and IL-4 in the culture supernatant were measured by ELISA.
[b] Mite extract (2) Preparation of a Subtracted cDNA Library Poly (A)+ RNA was respectively purified from the human Th1 clones (2P15) and the human Th2 clones (2P26) obtained in (1), by a customary method making use of oligo dT latex (by Nippon Roche K.K.). While the poly (A)+ RNA was used as a template, about 300 ng of cDNA was generated for each poly (A)+ RNA through use of an oligo (dT) primer (by Pharmacia) and MMLV reverse transcriptase (by Pharmacia). Next, to cut each cDNA into a strand length suitable for an amplifying process of the PCR method, the cDNA was digested for five hours at 37° C. through use of restriction enzymes AluI (by Toyobo) (84U) and a restriction enzyme RsaI (by Toyobo) (48U), whereby each of the following PCR linkers which have different nucleotide sequences each other was linked with each cDNA [Balzer, H. J., and Baumlein, H., Nucleic Acids Res., 22, 2853 (1994)]:

Linker for human Th1:

5'-CTC TTG CTT GAA TTC GGA CTA-3'   (Sequence ID No. 1)

3'-ACAC GAG AAC GAA CTT AAG CCT
    GAT-5'   (Sequence ID No. 2)

Linker for human Th2:

5'-AGT TAC ACG TCT AGA ATG GCT-3'   (Sequence ID No. 3)

3'-ATAG TCA ATG TGC AGA TCT TAC
    CGA-5'   (Sequence ID No. 4)

Only the cDNA fragments having the molecular-weight range from 0.2 Kbp to 2 Kbp were collected after fractionation by agarose gel electrophoresis. The thus-obtained 2P15-derived cDNA fragments and the 2P26-derived cDNA fragments were amplified by the PCR method through use of the following unique PCR primers (30 heat cycles each comprising: 94° C.×1 min.+50° C.×1 min.+72° C.×2 min.):

Primer for human Th1:

5'-CTC TTG CTT GAA TTC GGA CTA-3'   (Sequence ID No. 1)

Primer for human Th2:

5'-AGT TAC ACG TCT AGA ATG GCT-3'   (Sequence ID No. 3)

PCR products resulting from the PCR reaction were used as starting materials for subtraction purposes.

An excessive amount of the PCR products (100 μg) derived from the biotin-labeled human Th2 (2P26) was added to the PCR products (5 μg) derived from the human Th1 (2P15). [Photoreactive biotin (100 μg) (by Vector Laboratories) was added to DNA (100 μg). The mixture was placed stationary about 15 cm below a 160W Sun Lamp while being cooled on ice. The mixture was exposed to light for 15 mins. The non-reacted biotin was eliminated from the PCR product by butanol extraction. After repetition of these operations, biotinylated DNA was dissolved in Tris-EDTA buffer (TE), whereby labeling of the biotin was completed.] The resultant mixture was subjected to thermal denaturation at 100° C., so that each PCR product was dissociated into a single strand. The strands were hybridized with each other at 63° C. Next, 100 μg of streptavidin (by Life Technologies) was added to the system. Biotinylated 2P26-derived DNA and 2P15-derived cDNA that is hybridized with biotinylated 2P26-derived cDNA were absorbed to streptavidin, and the cDNA was eliminated from the system by extraction with phenol-chloroform. As a result of extraction, the cDNA containing a nucleotide sequence common to the cDNA derived from 2P26 was subtracted from the cDNA derived from 2P15, whereby subtraction for concentrating the 2P15-specific cDNA was completed.

The thus-concentrated 2P15-specific cDNA was repeatedly subjected to PCR amplification and subtraction twice. After the cDNA specific for 2P15 had been concentrated further, it was subjected to PCR amplification in the same way as described above.

The thus-prepared 2P15-specific cDNA was inserted to plasmidpBlue script SK(-) (by Stratagene), thereby completing preparation of a subtract cDNA library. Subsequently, a portion of the subtract cDNA library was used to transform E. coli (E. coli JM 109 strain).

(3) Isolation of the Th1 Gene Fragments

The 2P15-derived and 2P26-derived subtracted cDNA that were obtained in step (2) were labeled with $^{32}$P through use of a commercially available random primer labeling kit (by Takara), so that they were formed into radioactive probes.

Independently, the E. coli that had been transformed by part of the 2P15-derived cDNA library prepared in step (2) was seeded onto the plate. Two pairs of replica filters were formed with respect to colonies grown on the plate. These two pairs of replica filters were subjected to hybridization with the above-described two types of radioactive probes. They were washed with 0.1×SSC, and E. coli colonies containing cDNA homologous with the cDNA present in the probes were identified by autoradiography.

As a result of the screening of about 2,100 colonies according to this method, there were observed 320 colonies that did not provide a positive signal with respect to the subtracted 2P26-derived cDNA probe but provided a positive signal with respect to the subtracted 2P15-derived cDNA probe. With regard to these 320 cDNA clones, the difference between them was examined by a colony hybridization technique, whereby 33 independent clones which were not hybridized with one another were obtained.

For these 33 clones, the difference between 2P15 and 2P26 with regard to expression of these mRNAs was examined by the Northern blotting technique using the total RNA.

As a result, there were obtained 14 types of clones which indicate mRNA expression on 2P15 but not on 2P26.

To check the specificity of the cDNAs of the 14 types of clones against the human Th1, the difference in expression of mRNA between the plurality of human Th1 clone cells and human Th2 clone cells was examined by use of the Northern blotting technique. As a result, there were obtained several cDNA clones which were observed to have specificity in common for only the human Th1 clone cells. FIG. 1 illustrates the results of Northern blotting of one (T48) of these clones.

In FIG. 1, it is evident that T48 mRNA has expressed in the aforementioned two human Th1 clones (1P04 and 2P15; corresponding to lanes 1 and 2, respectively).

In contrast, T48 mRNA has not expressed in the human Th2 clone (2P26 and KND4; corresponding to lanes 3 and 4, respectively).

The nucleotide sequence of cDNA clone T48 has been analyzed according to the dideoxy termination method making use of a fluorescent terminator (a kit manufactured by Perkin Elmer was used).

It was revealed that the clone T48 had DNA of a novel nucleotide sequence.

A cDNA [Th1 gene of the present invention] containing a nucleotide sequence homologous with the above-described gene of clone T48 was cloned over its entire length.

(4) Cloning of the Th1 gene

In order to have the full length of the cDNA of interest cloned, a λphage cDNA library was produced from cells which induce a high level of expression of T48 mRNA.

Briefly, the total RNA was extracted from the 2P15 cells, and poly(A)$^+$ RNA was purified by a routine method through use of oligo (dT) latex (Nippon Roche K.K.). Next, double-stranded cDNA was synthesized through use of a commercially available cDNA cloning kit (by Life Technologies), and the thus-synthesized cDNA was cloned at the SalI/NotI site of λgt22A phages. Subsequently, the in vitro packaging of the λphages was completed through use of a commercially available kit (by Stratagene). The packaged products were infected with E. coli strain Y1090r$^-$, whereby about 2×10$^5$ recombinant λphages were obtained. The new cDNA fragments obtained in step (3) were labeled with $^{32}$P through use of a commercially available random primer labeling kit (by Takara). The labeled fragments, serving as radioactive probes, were used for the screening of the λphage library by the plaque hybridization method.

As a result, 13 positive cDNA clones were obtained. Of these positive cDNA clones, three clones having the longest insert DNA were selected, and subcloned at the EcoRV/NotI site of plasmid pBluescript SK(-) (by Stratagene).

As a result of the nucleotide sequence analysis performed according to the dideoxy termination method that used a fluorescent terminator similar to that used in (3), it was confirmed that nucleotide sequences located in the overlapping areas between the three positive clones of cDNA completely matched up with one another, and that they had been derived from the same gene.

Of these three positive clones, the clone T48-4 having the longest cDNA was named T48 and used in the following procedures.

(5) Structure of the Th1 gene of the Present Invention cDNA incorporated into the clone T48 has a strand length of 1153 bp, which is close to the length of the mRNA (about 1.4 kbp) determined by the Northern blotting technique. The cDNA has at its 3'-terminal a poly(A)$^+$ additional signal and fifteen A's (adenine) which seem to be a complementary sequence of oligo dT used in the reverse transcription reaction.

It was expected that the longest open reading frame would start with ATG, the 79th from the 5'-terminal end, and terminate at the 748th TGA and would encode a protein consisting of 223 amino acid residues. The nucleotide sequence (TCGCCATGA) in the vicinity of the initiation codon of the gene was substantially homologous with the consensus sequence (CCA(G)CCATGG of Kozak (Kozak, M., Nucleic Acids Res., 15, 8125 (1987)).

In view of the foregoing descriptions, the clone T48 was determined to contain substantially the full length of cDNA which starts from the 3'-terminal and reaches up to a part of the untranslated region on the 5'-terminal side via the full length of the coding region.

The gene having the cDNA of clone T48 is taken as the Th1 gene of the present invention, and the sequence of this gene is represented by sequence ID No. 5. Further, an amino acid sequence deduced to be encoded by this nucleotide sequence is represented by sequence ID No. 6.

The amino acid sequence is expressed by the single letter representation method as follows.

[MKFVPCLLLVTLSCLGTLGQAPRQKQGSTGEEFHFQTGGRDSCTMRPSSLGQGAGEVWLRVDCR

NTDQTYWCEYRGQPSMCQAFAADPKPYWNQALQELRRLHHACQGAPVLRPSVCREAGPQAHMQQ

VTSSLKGSPEPNQQPEAGTPSLRPKATVKLTEATQLGKDSMEELGKAKPTTRPTAKPTQPGPRP

GGNEEAKKKAWEHCWKPFQALCAFLISFFRG]

[In the above-described amino acid sequence, A: alanine, V: valine, L: leucine, I: isoleucine, P: proline, F: phenylalanine, W: tryptophan, M: methionine, G: glycine, S: serine, T: threonine, C: cysteine, Q: glutamine, N: asparagine, Y: tyrosine, K: lysine, R: arginine, H: histidine, D: aspartic acid, and E: glutamic acid]

The transformant prepared by integrating the gene of the present invention into *E. coli* (*E. coli* K12-JM109 strain) is deposited with the National Institute of Bioscience and Human Technology, Agency of Industrial Science and Technology, Japan Ministry of International Trade and Industry (deposition No. FERM P-15618).

(6) In vitro Transcription and Translation of Th1 gene

While the Th1 gene of the present invention was used as a template, RNA was synthesized with T7 RNA polymerase through use of a commercially available kit (by Stratagene) and T7RNA polymerase. Subsequently, the RNA was translated in vitro in the presence of $^{35}$S-methionine through use of commercially available rabbit reticulocytes (by Promega Biotech).

Figure 2:
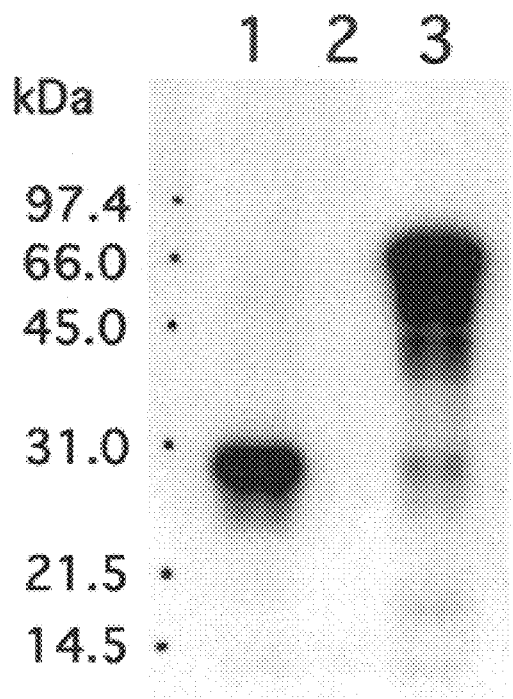
FIG. 2 is an autoradigram showing an in vitro translation product of the Th1 gene of the present invention.

According to the Laemmli method, the thus-translated product was analyzed by SDS polyacrylamide gel electrophoresis. As a result, it was confirmed that there had been formed a single protein having a molecular weight which is similar to the predicted molecular weight of 25 kd had been formed (see FIG. 2).

(7) Tissue Specificity of Expression of mRNA

To examine the tissue specificity of expression of the mRNA derived from the Th1 gene of the present invention, the total RNA of cell lines derived from various tissues was subjected to Northern blot analysis.

Figure 3:
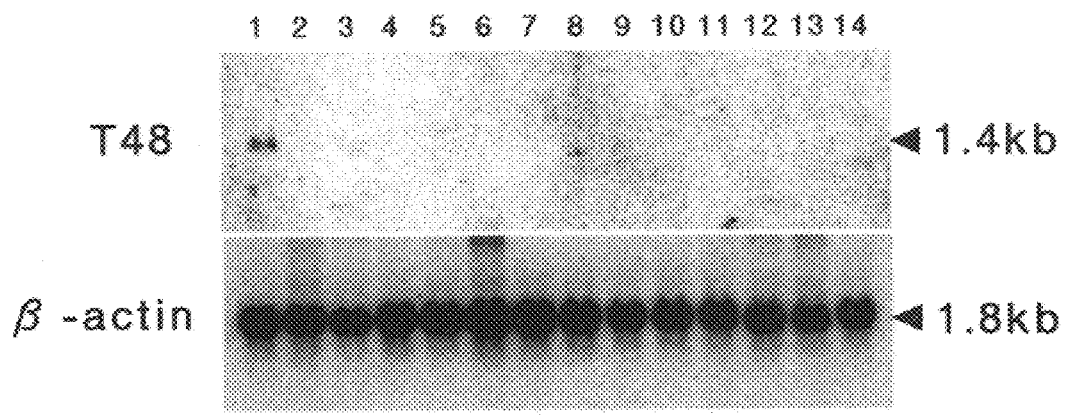
FIG. 3 is an autoradigram photograph showing the results of a Northern blot analysis which indicate the tissue specificity of expression of mRNA derived from the Th1 gene of the present invention.

As a result, expression of the mRNA derived from the Th1 gene could not be confirmed in any of the cell lines (FIG. 3).

Thus, it has become evident that expression of the Th1 gene is limited to a specific cell that includes the Th1 cells.

EXAMPLE 2

Manufacture of *E. coli* Recombinant Th1 Protein (1) Manufacture of Th1 gene expression vector While a plasmid DNA (pBluescript SK(−)) containing the full length of the Th1 gene of the present invention was used as a template, a gene region encoding the central portion of the human Th1 protein of the present invention which corresponds to the protein in which 19 amino acid residues on the N-terminal side and 20 amino acid residues on the C-terminal side had been deleted from the intact protein was amplified by PCR through use of a sense primer which contained a BamHI site and a nucleotide sequence encoding an enterokinase recognition cutting site [5'-CGA GGA TCC GAT GAC GAT GAC A AA CAG GCC CCG AGA CAA AAG CAA-3' (sequence ID No. 7)] and an anti-sense primer [5'-CC A ACA AGC TTA CCA GGC CTT CTT CTT TG C TTC-3' (sequence ID No. 8)] which contained a HindIII site.

In the PCR processing, a heating operation was performed for 10 cycles (one heat cycle comprised: 96°×30 sec.+60° C.×1 min.+76° C.×3 min.) through use of heat resistant DNA polymerase (by Stratagene). The resultant PCR product was purified by phenol-chloroform extraction and ethanol precipitation, and the thus-purified product was digested with restriction enzymes (BamHI and HindIII). The digested product was purified by agarose gel electrophoresis. The purified DNA was inserted at the BamHI/HindIII site of pQE 30 (by Qiagen), whereby expression plasmid pQE/T48 for use with *E. coli* of interest was obtained.

(2) Manufacture of Recombinant Human Th1 Protein of the Present Invention

To obtain the recombinant human Th1 protein of the present invention, the *E. coli* M15 was transformed by the expression plasmid pQE/T48. The transformant was subjected to shaking culture overnight in 20 ml of a TB medium at 37° C. The thus-obtained culture product was inoculated into a TB medium (1 liter), and continuously cultured at 37° C. When an absorbance was 1.0 at 600 nm, IPTG (by Sigma) was added to the transformant culture, so that the final concentration of the IPTG became 0.2 mM. The transformant was further subjected to shaking culture for three hours. The culture product was subjected to centrifugal processing and cells were collected. Then the cells were suspended in 40 ml of a binding solution (8M urea, 100 mM $NaH_2PO_4$, 10 mM Tris-HCl, pH 8.0). The suspension was stirred at room temperature for 1 hour. After completion of stirring, the resultant cell lysate was subjected to centrifugal separation (10,000×g, 15 min., 4° C.). 16 ml of Ni-NTA Resin (by Qiagen) equilibrated in advance with the binding solution were added to the centrifugal supernatant, and then stirred for 1.5 hours at room temperature.

The Ni-NTA Resin after binding reaction was thoroughly washed with the binding solution and a washing solution (prepared by adjusting the pH of the binding solution to 6.3), packed in a column, and eluted by use of 0–300 mM imidazole gradient in the washing solution. The eluent was fractionated in volumes of 2 ml.

Fractions corresponding to elution peaks were pooled. From the pool, urea was gradually removed through dialysis. Finally, the pool was subjected to a dialysis against 50 mM Tris-HCl (pH 7.3), 150 mM NaCl, and 10% glycerol buffer, to thereby obtain the target recombinant human Th1 protein of the present invention.

Figure 4:
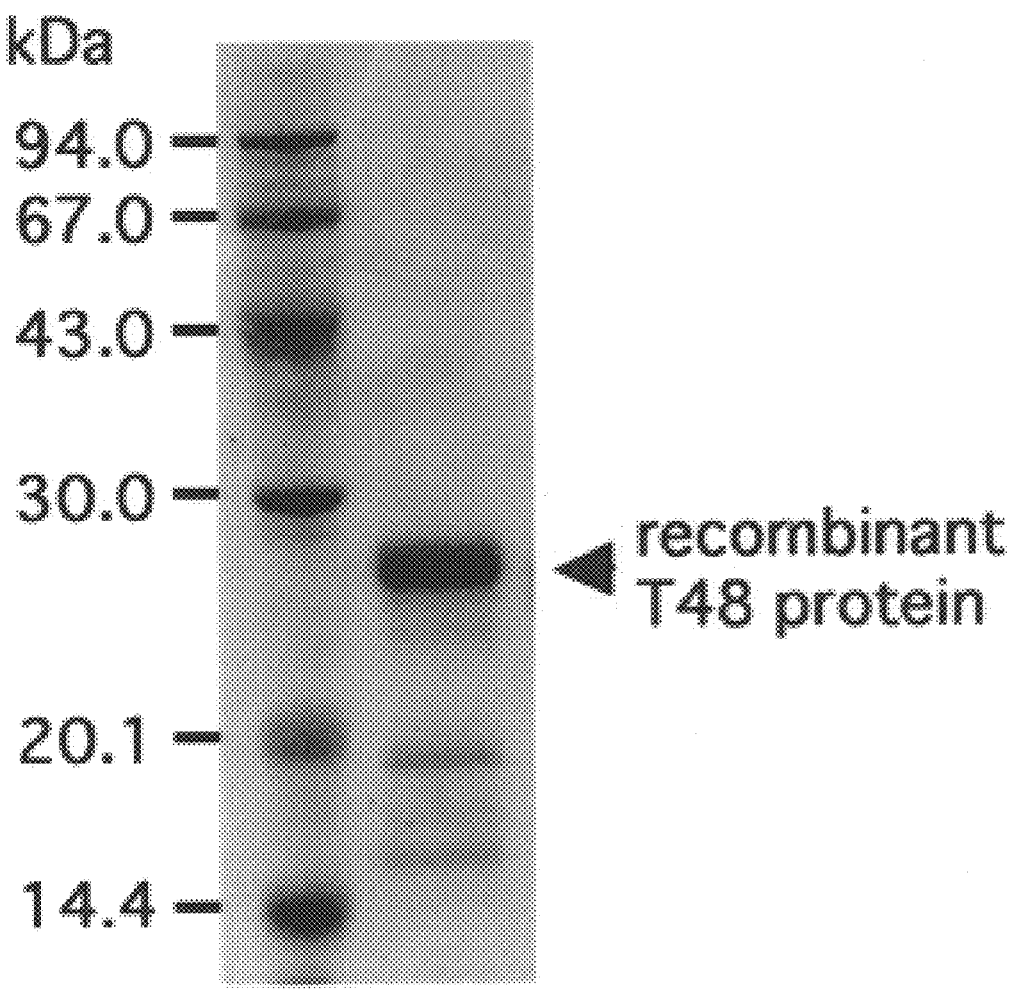
FIG. 4 shows the results of reducing SDS polyacrylamide gel electrophoresis performed on the recombinant human-Th1 protein of the present invention.

The thus-prepared recombinant Th1 protein of the present invention was analyzed by SDS polyacrylamide gel electrophoresis under reducing conditions. The results are shown in FIG. 4.

EXAMPLE 3

Manufacture of a Monoclonal Antibody against the Human Th1 Protein (1) Preparation of the Mammalian Expression Vector for the Th1 Gene of the Present Invention and Genetic Immunization E. coli (E. coli K12-JM109) transformed with a plasmid DNA (pBluescript SK(-)) containing the full length of the Th1 gene of the present invention (sequence ID No. 5) (the aforementioned T48 cDNA) was proliferated. From the cells collected, plasmid DNA was extracted and digested with restriction enzymes HindIII and NotI. Vector DNA was separated on agarose gel by electrophoresis, to thereby prepare an insert DNA (T48). The thus-obtained T48 gene (from 78 bp upstream of the initiation codon to the poly A tail) was inserted between the HindIII site and the NotI site located on the downstream side of a cytomegarovirus promotor of pRc/CMV plasmid (by Invitrogen), obtaining a plasmid DNA (pRc/CMV-T48) which integrated the full length of T48.

A physiological saline solution of the thus-obtained pRc/CMV-T48 was intramuscularly injected into both quadriceps of each of 8-weeks-old female BALB/c mice and also intradermally injected into the tail of each mouse (20 μg for each site; a total of 60 μg for 1 mouse at each time). This procedure was performed three times in total at intervals of three weeks, to thereby immunize the mice. The rise of titre by the specific antibody in the immune sera was confirmed through the indirect fluorescent antibody technique and the Western blotting technique. Subsequently, boosters were administered twice to each of the animal in a similar manner.

(2) Preparation of Hybridoma

Two weeks after the final immunization, spleen cells ($1 \times 10^8$ cells) of each immunized mouse and myeloma cells ($3 \times 10^7$ cells) were mixed in an RPMI 1640 medium. Thereafter, a pellet of mixed cells obtained by centrifugal separation of the mixture was washed with an RPMI 1640 medium and the supernatant was completely removed. To the residual pellet was added, over 45 seconds and with stirring, a 37° C. prewarmed 50% polyethylene glycol (average molecular weight: 1,500) PBS solution, followed by gentle mixing. An RPMI 1640 medium (30 ml) was added so as to uniformly suspend the cells. Subsequently, the system was subjected to centrifugal separation, to thereby reprecipitate the cells.

The thus-obtained cells were suspended in a HAT medium, and seeded in the wells of a 96-well plate at a density of $1 \times 10^5$ cells/50 μl of suspension per well. The cells were incubated at 37° C. in 5% $CO_2$. On days 5, 7, and 9 following the start of incubation, 50 μl of a HAT medium was added to each well so as to supplement nutrients, and the cells were observed. Between the 10th and 14th days of culturing, proliferation of cells was observed in almost all wells. A predetermined volume of the culture supernatant was collected from each well and subjected to a primary screening procedure. Briefly, the supernatant was reacted, at room temperature for 30 minutes, with COS7 cells which had been fixed and permeabilized on a slide and which were forced to express T48-derived cDNA. [The COS7 cells used in this procedure were pcDL-SRa/COS7 prepared as follows. On COS7 cells that had been cultured for 18 hours in DMEM containing 10% fetal bovine serum (FBS) was placed a layer of an Opti-MEM I medium (by Life Technologies) containing a mixture of a lipofectin reagent (by Life Technologies) and pcDL-SRa plasmid DNA integrated with T48-derived cDNA, and incubated at 37° C. for 6 hours. Subsequently, the medium was removed from the culture, and in its place 10% FBS/DMEM was added, followed by incubation at 37° C. for 42 hours.] The reaction system was washed and allowed to react with FITC-labeled goat anti-mouse IgG at room temperature for 30 minutes under light-shielded conditions. The reaction system was washed again, covered with a cover glass, and then observed under a fluorescent microscope.

The slide used herein was prepared as follows.

Briefly, COS7 cells (see above) which were forced to express T48-derived cDNA were suspended in 10% FBS/DMEM at a density of $5 \times 10^5$ cells/ml, and the resultant suspension was spotted onto a 12-well-spot slide glass (40 μl/well). The slide glass was placed in an incubator, and the cells were incubated at 37° C. for 3 hours, to thereby cause the cells to adhere onto the slide glass. The slide was then gently rinsed with PBS and treated with ice-cold 2% paraformaldehyde/PBS solution at room temperature for 10 minutes so as to immobilize the cells. The fixed cells were rinsed with PBS again, and treated with 0.1% Nonidet P-40 solution at room temperature for 5 minutes to solubilize the cytoplasmic membrane, thereby completing preparation of the slide.

(3) Preparation of Monoclonal Antibodies

The cells in the wells that reacted only with the cells integrated with T48-derived cDNA in Example 2 above were subjected to a limiting dilution method for selecting monoclones, as well as to a secondary screening procedure.

Selection of monoclones was performed as follows. First, the number of cells in those wells was counted. A medium comprising a suspension of the cells was dispensed into the wells of a 96-well plate at a density of 0.2 cells/well, follows by culturing. The culture supernatant was that used in the aforementioned screening procedure. This process was repeated twice.

The secondary screening was performed as follows.

(1) Immunoblotting method:

The COS7 cells that had been forced to express T48-derived cDNA (see above) were lysed in a buffer that contained 0.5% Nonidet P-40. The resultant solution was subjected to centrifugal separation to remove nuclei and the supernatant was collected as a sample. The sample was subjected to SDS polyacrylamide gel electrophoresis under reducing or non-reducing conditions.

The protein in the electrophoresis gel were transferred onto a nitrocellulose membrane, and the nitrocellulose membrane was soaked in a blocking buffer (PBS which contained 1% skim milk, 5% FBS, and 0.1% Tween 20). After being allowed to stand at 4° C. overnight, the membrane was soaked in a culture supernatant of the hybridoma, and reacted at room temperature for 1 hour. The membrane was washed in a wash buffer (0.1% Tween 20-containing PBS) for 15 minutes. After being washed three times, the membrane was reacted with diluted labeled secondary antibodies (horseradish peroxidase-labeled goat anti-mouse IgG antibody) at room temperature for 1 hour. Subsequently, the membrane was washed with a wash buffer three times, and was then subjected to a chemiluminescence technique. Bands were detected with a film for autoradiography.

(2) Flow cytometry (this technique is useful when the antigen protein is expressed on the cell-surface membrane):

The COS7 cells that had been forced to express T48-derived cDNA were suspended in a hybridoma supernatant which had been suitably diluted with 10% FBS/RPMI 1640 medium, and allowed to react therewith for 30 minutes on ice. The cells were washed twice with a wash buffer (PBS which contained 0.1% BSA and 0.05% NaN₃), and were then reacted with a diluted FITC-labeled goat anti-mouse IgG antibody for 30 minutes on ice. Subsequently, the cells were washed with a wash buffer twice, suspended in PBS, and subjected to flow cytometry for detecting fluorescence.

By culturing the thus-selected hybridoma that produce the Th1-gene-product-specific monoclonal antibodies of the present invention, antibodies were purified from the culture medium, to thereby obtain the target human Th1-specific monoclonal antibody.

Also, the hybridomas were administered into the abdominal cavity of a BALB/c mouse, to thereby allow the cells to proliferate in the abdominal cavity. After the ascites containing the antibodies had accumulated, the ascites were collected and the antibodies were purified. From the above procedures, mouse hybridoma clones TDA-3 and TFG-7 which produce the human Th1 protein-specific monoclonal antibody of the present invention were obtained.

Figure 5:
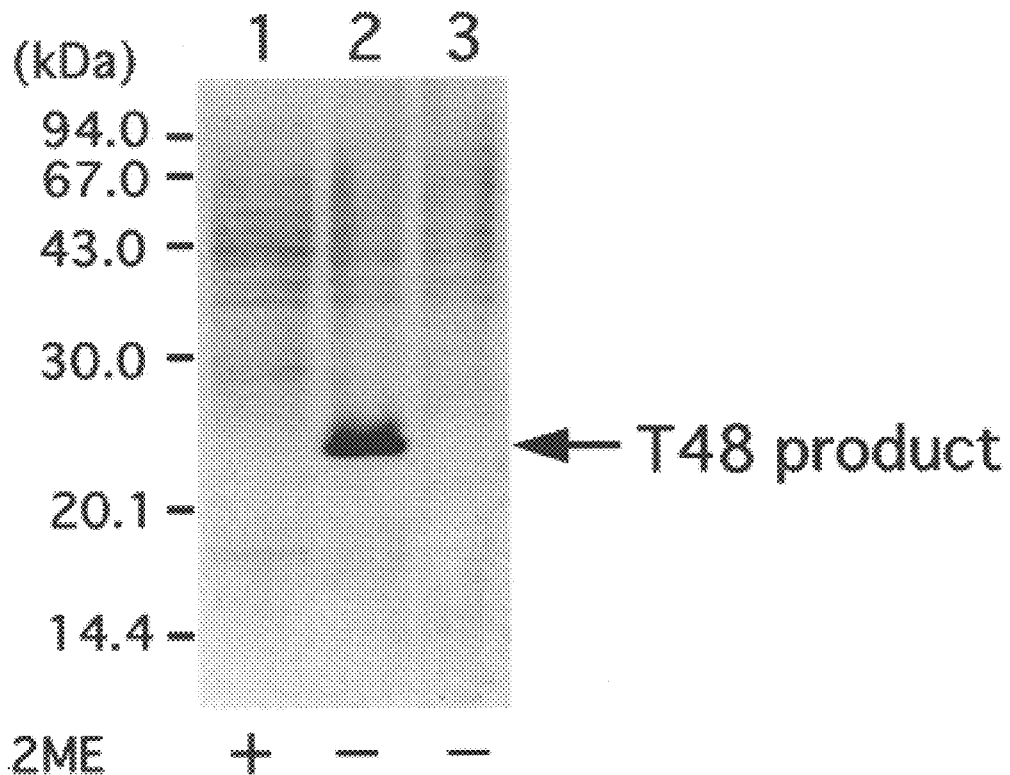
FIG. 5 shows the results of immunoblotting performed on COS7 cells with a monoclonal antibody produced by mouse hybridoma TDA-3, in which cDNA derived from T48 was forcibly expressed.
Figure 6A:
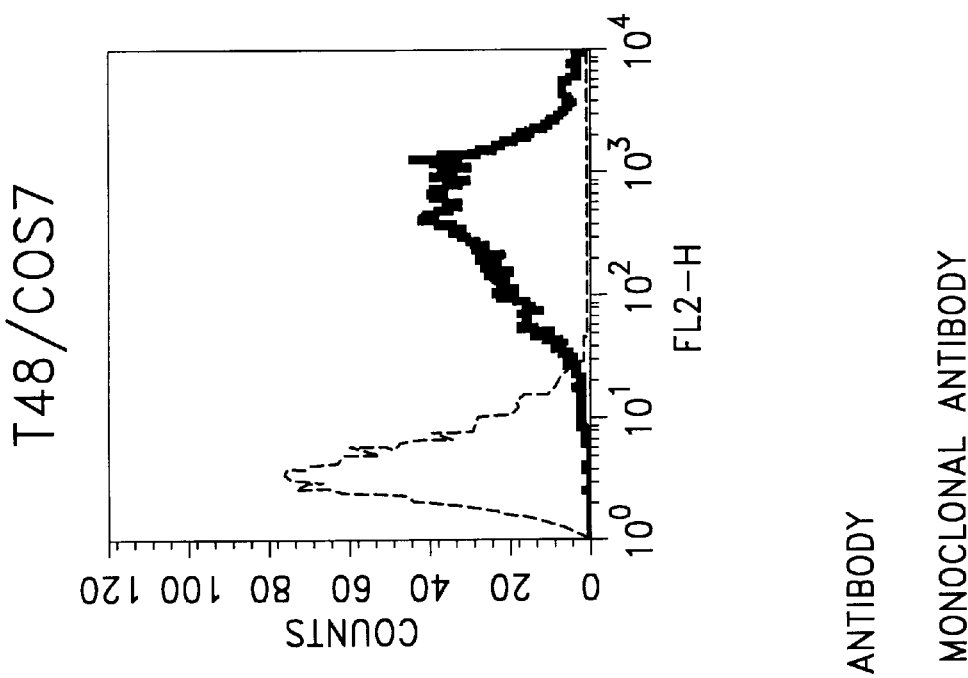
FIG. 6 shows the results of flow cytometry performed on COS7 cells, stained with a monoclonal antibody produced by mouse hybridoma TDA-3, in which cDNA derived from T48 was forcibly expressed.
Figure 6B:
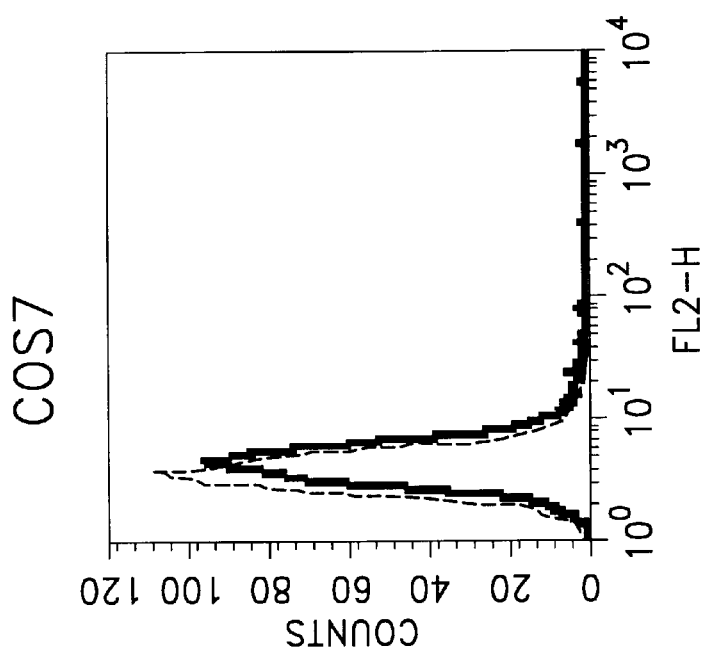

FIG. 5 shows the results obtained by immunoblotting of COS7 cells that were forced to express T48-derived cDNA by use of the monoclonal antibody which was produced by clone TDA-3 of the above two types of clones. Also, FIG. 6 shows the results of a flow cytometry analysis performed on the same cells.

The hybridomas that produce monoclonal antibodies specific to the human Th1 protein of the present invention have been deposited with the National Institute of Bioscience and Human Technology, Agency of Industrial Science and Technology, Japan Ministry of International Trade and Industry, as Mouse Hybridoma TDA-3 and Mouse Hybridoma TFG-7 (the deposit numbers are FERM P-16033 for Mouse Hybridoma TDA-3 and FERM P-16034 for Mouse Hybridoma TFG-7).

EXAMPLE 4

Expression of the Human Th1 Protein of the Present Invention on Polyclonal, Short-term Cultured Peripheral Blood Mononuclear Cells (1) Preparation of polyclonal, short-term cultured peripheral blood mononuclear cells Peripheral blood mononuclear cells (PBMCs) from a healthy human were incubated for four days in a 10% FBS/RPMI 1640 medium (by Life Technologies) supplemented with 5 μg/ml of PPD (by Japan BCG Manufacturing Co.), 50 ng/ml of rIFN-γ, and 5 ng/ml of rIL-12, so as to primarily induce human Th1 cells.

Independently, PBMCs were incubated for four days in a 10% FBS/RPMI 1640 medium supplemented with 1% (v/v) of a mite extract, 1% (v/v) of a house dust extract (by Torii), 100 ng/ml of rIL-4, and 10 μg/ml of anti-IFN-γ monoclonal antibody, so as to primarily induce human Th2 cells.

Four days thereafter, 50 U/ml of rIL-2 was added to each culture, and incubation was continued for additional 6–10 days.

(2) Expression analysis of the human Th1 protein of the present invention by flow cytometry The thus-obtained polyclonal, short-term incubated PBMCs were cultured overnight in an AIMV medium (by Life Technologies), and stained by the membrane fluorescent antibody method through use of one type of the monoclonal antibodies; i.e., mouse hybridoma TDA3-derived monoclonal antibodies. Briefly, $10^5$ PBMCs were suspended in 50 μl of a staining solution* containing 5 μg/ml of monoclonal antibody TDA3 (*: PBS containing 5% fetal bovine serum, 5% goat serum, 1% BSA, and 0.05% sodium azide) for causing a reaction for 30 minutes on ice. After completion of reaction, the cells were washed twice with a wash buffer (PBS containing 0.5% BSA and 0.05% sodium azide), suspended in 50 μl of a staining solution containing 2 μl/ml of phycoerythrin-labeled goat anti-mouse IgG antibody (by Chemicon), to thereby cause a reaction for 30 minutes on ice. After two washings, the cells were subjected to an analysis by flow cytometry (FACScan, by Becton Dickinson).

Figure 7A:
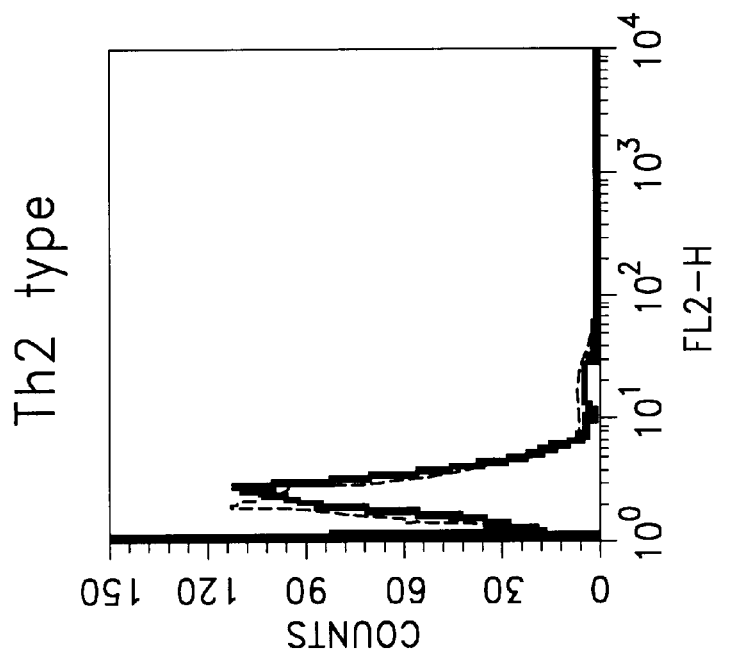
FIG. 7 shows the results of flow cytometry performed on polyclonal short-term cultured PBMCs stained by membrane immunofluorescence technique with a monoclonal antibody produced by mouse hybridoma TDA-3.
Figure 7B:
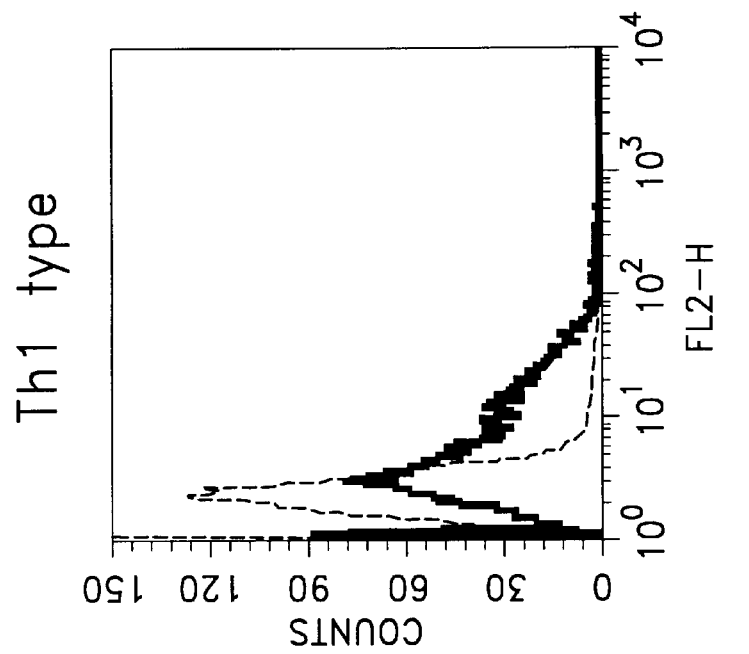

The results are shown in FIG. 7.

As shown in FIG. 7, the human Th1 protein of the present invention was confirmed to have been expressed on the cell-surface membrane, and the expression was dominant over the short-term cultured PBMCs of the Th1 type.

By virtue of the present invention, there are provided a human-Th1-specific gene and a human-Th1-specific protein which are important factors of means for specifying the condition and type of immune-related diseases on the basis of the knowledge about the polarization of distribution of Th1/Th2 subsets.

Further, there are provided a recombinant expression vector which contains the human-Th1-specific gene and a transformant which is transformed by the above-described recombinant vector.

There are provided monoclonal and polyclonal antibodies which recognize the human-Th1-specific protein as an antigen, and a hybridoma which produces these monoclonal antibodies.

What is claimed is:

1. An isolated human-Th1-specific protein having the amino acid sequence listed as SEQ ID NO: 6.

2. An isolated human Th1-specific protein existing in human Th1 cells but not in human Th2 cells said protein (a) exhibiting substantially the same biological activities as the human-Th1-specific protein according to claim 1 and (b) said protein being encoded by a polynucleotide sequence which hybridizes under stringent conditions with the nucleic acid sequence of SEQ ID NO: 5.

3. An isolated human-Th1-specific polynucleotide having a nucleotide sequence coding for the amino acid sequence listed as SEQ ID NO: 6.

4. An isolated human-Th1-specific polynucleotide having the nucleic acid sequence listed as SEQ ID NO: 5.

5. An isolated human polynucleotide sequence encoding an isolated Th-1-specific protein of claim 2, said polynucleotide sequence hybridizing under stringent conditions with the nucleic acid sequence of SEQ ID NO: 5.

6. A recombinant expression vector comprising the human-Th1-specific polynucleotide according to claim 3.

7. A recombinant expression vector comprising the human-Th1-specific polynucleotide according to claim 4.

8. A recombinant expression vector comprising the human-Th1-specific polynucleotide according to claim 5.

9. A transformant transformed by the recombinant vector according to claim 6, wherein the human-Th1-specific polynucleotide contained in the recombinant vector is expressed.

10. A transformant transformed by the recombinant vector according to claim 7, wherein the human-Th1-specific polynucleotide contained in the recombinant vector is expressed.

11. A transformant transformed by the recombinant vector according to claim 8, wherein the human-Th1-specific polynucleotide contained in the recombinant vector is expressed.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: Other (xi) SEQUENCE DESCRIPTION: SEQ ID NO:1:

CTCTTGCTTG AATTCGGACT A                                                    21

(2) INFORMATION FOR SEQ ID NO:2:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:2:

TAGTCCGAAT TCAAGCAAGA GCACA                                                25

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:3:

AGTTACACGT CTAGAATGGC T                                                    21

(2) INFORMATION FOR SEQ ID NO:4:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:4:

AGCCATTCTA GACGTGTAAC TGATA                                                25

(2) INFORMATION FOR SEQ ID NO:5:

(i) SEQUENCE CHARACTERISTICS:
        (A) LENGTH: 1153 base pairs
        (B) TYPE: nucleic acid
        (C) STRANDEDNESS: both
        (D) TOPOLOGY: unknown (ii) MOLECULE TYPE: cDNA to mRNA (xi) SEQUENCE DESCRIPTION: SEQ ID NO:5:

CCCTTTAAAG GGTGACTCGT CCCACTTGTG TTCTCTCTCC TGGTGCAGAG TTGCAAGCAA    60

GTTTATCAGA GTATCGCCAT GAAGTTCGTC CCCTGCCTCC TGCTGGTGAC CTTGTCCTGC   120

CTGGGGACTT TGGGTCAGGC CCCGAGGCAA AAGCAAGGAA GCACTGGGGA GGAATTCCAT   180

TTCCAGACTG GAGGGAGAGA TTCCTGCACT ATGCGTCCCA GCAGCTTGGG GCAAGGTGCT   240

GGAGAAGTCT GGCTTCGCGT CGACTGCCGC AACACAGACC AGACCTACTG GTGTGAGTAC   300

AGGGGGCAGC CCAGCATGTG CCAGGCTTTT GCTGCTGACC CCAAACCTTA CTGGAATCAA   360

GCCCTGCAGG AGCTGAGGCG CCTTCACCAT GCGTGCCAGG GGGCCCCGGT GCTTAGGCCA   420

TCCGTGTGCA GGGAGGCTGG ACCCCAGGCC CATATGCAGC AGGTGACTTC CAGCCTCAAG   480

-continued

```
GGCAGCCCAG AGCCCAACCA GCAGCCTGAG GCTGGGACGC CATCTCTGAG GCCCAAGGCC      540

ACAGTGAAAC TCACAGAAGC AACACAGCTG GGAAAGGACT CGATGGAAGA GCTGGGAAAA      600

GCCAAACCCA CCACCCGACC CACAGCCAAA CCTACCCAGC CTGGACCCAG GCCCGGAGGG      660

AATGAGGAAG CAAAGAAGAA GGCCTGGGAA CATTGTTGGA AACCCTTCCA GGCCCTGTGC      720

GCCTTTCTCA TCAGCTTCTT CCGAGGGTGA CAGGTGAAAG ACCCCTACAG ATCTGACCTC      780

TCCCTGACAG ACAACCATCT CTTTTTATAT TATGCCGCTT TCAATCCAAC GTTCTCACAC      840

TGGAAGAAGA GAGTTTCTAA TCAGATGCAA CGGCCCAAAT TCTTGATCTG CAGCTTCTCT      900

GAAGTTTGGA AAAGAAACCT TCCTTTCTGG AGTTTGCAGA GTTCAGCAAT ATGATAGGGA      960

ACAGGTGCTG ATGGGCCCAA GAGTGACAAG CATACACAAC TACTTATTAT CTGTAGAAGT     1020

TTTGCTTTGT TGATCTGAGC CTTCTATGAA AGTTTAAATA TGTAACGCAT TCATGAATTT     1080

CCAGTGTTCA GTAAATAGCA GCTATGTGTG TGCAAAATAA AGAATGATT TCAGAAATAA      1140

AAAAAAAAAA AAA                                                        1153
```

(2) INFORMATION FOR SEQ ID NO:6:

(i) SEQUENCE CHARACTERISTICS:
        (A) LENGTH: 223 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO:6:

```
Met Lys Phe Val Pro Cys Leu Leu Val Thr Leu Ser Cys Leu Gly
 1               5                  10                  15

Thr Leu Gly Gln Ala Pro Arg Gln Lys Gln Gly Ser Thr Gly Glu Glu
             20                  25                  30

Phe His Phe Gln Thr Gly Gly Arg Asp Ser Cys Thr Met Arg Pro Ser
             35                  40                  45

Ser Leu Gly Gln Gly Ala Gly Glu Val Trp Leu Arg Val Asp Cys Arg
         50                  55                  60

Asn Thr Asp Gln Thr Tyr Trp Cys Glu Tyr Arg Gly Gln Pro Ser Met
65                  70                  75                  80

Cys Gln Ala Phe Ala Ala Asp Pro Lys Pro Tyr Trp Asn Gln Ala Leu
                     85                  90                  95

Gln Glu Leu Arg Arg Leu His His Ala Cys Gln Gly Ala Pro Val Leu
                100                 105                 110

Arg Pro Ser Val Cys Arg Glu Ala Gly Pro Gln Ala His Met Gln Gln
            115                 120                 125

Val Thr Ser Ser Leu Lys Gly Ser Pro Glu Pro Asn Gln Gln Pro Glu
        130                 135                 140

Ala Gly Thr Pro Ser Leu Arg Pro Lys Ala Thr Val Lys Leu Thr Glu
145                 150                 155                 160

Ala Thr Gln Leu Gly Lys Asp Ser Met Glu Glu Leu Gly Lys Ala Lys
                    165                 170                 175

Pro Thr Thr Arg Pro Thr Ala Lys Pro Thr Gln Pro Gly Pro Arg Pro
                180                 185                 190

Gly Gly Asn Glu Glu Ala Lys Lys Lys Ala Trp Glu His Cys Trp Lys
            195                 200                 205

Pro Phe Gln Ala Leu Cys Ala Phe Leu Ile Ser Phe Phe Arg Gly
        210                 215                 220
```

```
(2) INFORMATION FOR SEQ ID NO:7:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:7:

CGAGGATCCG ATGACGATGA CAAACAGGCC CCGAGACAAA AGCAA                    45

(2) INFORMATION FOR SEQ ID NO:8:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: Other (xi) SEQUENCE DESCRIPTION: SEQ ID NO:8:

CCAACAAGCT TACCAGGCCT TCTTCTTTGC TTC                                 33
```